(12) United States Patent
Fritz

(10) Patent No.: US 10,329,214 B2
(45) Date of Patent: Jun. 25, 2019

(54) METHOD AND APPARATUS FOR PRODUCING HYDROCARBONS

(71) Applicant: Linde Aktiengesellschaft, München (DE)

(72) Inventor: Helmut Fritz, München (DE)

(73) Assignee: Linde Aktiengesellschaft, Munich (DE)

( * ) Notice: Subject to any disclaimer, the term of this patent is extended or adjusted under 35 U.S.C. 154(b) by 0 days.

(21) Appl. No.: 15/533,002

(22) PCT Filed: Dec. 2, 2015

(86) PCT No.: PCT/EP2015/078302
§ 371 (c)(1),
(2) Date: Jun. 2, 2017

(87) PCT Pub. No.: WO2016/087491
PCT Pub. Date: Jun. 9, 2016

(65) Prior Publication Data
US 2017/0320793 A1    Nov. 9, 2017

(30) Foreign Application Priority Data

Dec. 5, 2014  (EP) .................... 14196643

(51) Int. Cl.
*C07C 2/82*   (2006.01)
*C07C 7/11*   (2006.01)
*F25J 3/02*   (2006.01)

(52) U.S. Cl.
CPC ............ *C07C 2/82* (2013.01); *C07C 7/11* (2013.01); *F25J 3/0209* (2013.01); *F25J 3/0219* (2013.01);
(Continued)

(58) Field of Classification Search
None
See application file for complete search history.

(56) References Cited

U.S. PATENT DOCUMENTS

2005/0218041 A1*  10/2005  Yoshida ........... B01D 3/14
                                                 208/340
2011/0067441 A1*   3/2011  Martinez ......... F25J 3/0209
                                                  62/620
(Continued)

FOREIGN PATENT DOCUMENTS

WO    1999061852 A1   12/1999
WO    2013106771 A2    7/2013
WO    2014011646 A1    1/2014

OTHER PUBLICATIONS

PCT/EP2015/078302 English translation of the Written Opinion of the International Search Authority, dated Feb. 8, 2016, 7 pages.
(Continued)

*Primary Examiner* — Philip Y Louie
(74) *Attorney, Agent, or Firm* — Lathrop Gage LLP

(57) ABSTRACT

A method for producing hydrocarbons is proposed, in which a product stream containing hydrocarbons is produced from a methane-rich feed stream and from an oxygen-rich feed stream in a reaction unit which is configured for implementing a method for oxidative coupling of methane, the product stream or at least a stream formed therefrom being treated cryogenically in at least one separation unit using at least one liquid, methane-rich stream. It is provided that in the at least one separation unit (10) a recycle stream is formed from methane contained in product stream (c) and from methane contained in the at least one liquid, methane-rich stream (e, v), the recycle stream being fed to the reaction unit (1) as the methane-rich feed stream (a), and in that the liquid, methane-rich stream (e, v) is provided as makeup.

10 Claims, 3 Drawing Sheets

(52) U.S. Cl.
CPC ........... *F25J 3/0233* (2013.01); *F25J 3/0238* (2013.01); *F25J 3/0252* (2013.01); *F25J 2200/02* (2013.01); *F25J 2200/04* (2013.01); *F25J 2200/72* (2013.01); *F25J 2200/74* (2013.01); *F25J 2200/78* (2013.01); *F25J 2200/96* (2013.01); *F25J 2205/04* (2013.01); *F25J 2205/50* (2013.01); *F25J 2210/02* (2013.01); *F25J 2210/12* (2013.01); *F25J 2210/62* (2013.01); *F25J 2215/04* (2013.01); *F25J 2215/60* (2013.01); *F25J 2270/904* (2013.01); *F25J 2290/50* (2013.01)

(56) References Cited

U.S. PATENT DOCUMENTS

| | | | | |
|---|---|---|---|---|
| 2011/0277500 | A1* | 11/2011 | Bauer | F25J 3/0209 62/630 |
| 2013/0225884 | A1* | 8/2013 | Weinberger | F25J 3/0219 585/16 |
| 2017/0137355 | A1* | 5/2017 | Sarsani | C01B 3/36 |

OTHER PUBLICATIONS

PCT/EP2015/078302 English translation of the International Search Report, dated Feb. 8, 2016, 2 pages.
PCT/EP2015/078302 English translation of the International Preliminary Report on Patentability, dated Jun. 13, 2017, 8 pages.
Eurasian Patent Application No. 201791027/31, English translation of Office Action dated Sep. 26, 2018, 2 pages.
Eurasian Patent Application No. 201791027/31, Office Action dated Sep. 26, 2018, 2 pages.

\* cited by examiner

METHOD AND APPARATUS FOR PRODUCING HYDROCARBONS

The invention relates to a method for producing hydrocarbons by oxidative coupling of methane according to the preamble of claim 1 and to a corresponding apparatus.

PRIOR ART

Methods for producing higher hydrocarbons from methane by oxidative coupling of methane (OCM) are presently undergoing intensive development. In oxidative coupling of methane, a methane-rich stream and an oxygen-rich stream are fed into a reactor where the oxygen of the oxygen-rich stream and a part of the methane of the methane-rich stream react to produce higher hydrocarbons, in particular the typical target product ethylene, whilst forming water and by-products.

Issuing from the reactor is a product stream which, due to the yields which are currently still low, contains relatively large proportions (more than 60%) of unreacted methane and relatively small proportions (less than 10%) of hydrocarbons having two or more carbon atoms. A corresponding product stream typically also contains 10 to 20% of other components such as nitrogen, argon, hydrogen, carbon monoxide and/or carbon dioxide. However, the invention is also suitable for use with product streams having higher contents of hydrocarbons with two or more carbon atoms.

Therefore, in principle as with product streams from other methods for producing hydrocarbons, a corresponding product stream also has to be at least partly separated into the components which are contained. This can be carried out using differently configured separation sequences to which a corresponding product stream is subjected after being suitably processed, for example following the separation of water and/or carbon dioxide and after compression.

Separation sequences are described for product streams from steam cracking processes in, for example the article "Ethylene" in Ullmann's Encyclopedia of Industrial Chemistry, Online edition, 15 Apr. 2007, DOI 10.1002/14356007.a10_045.pub2. Some of the separation steps used therefor can also be used in the separation sequences for oxidative coupling of methane, the focus here being on the separation of the large amounts of methane and on the recovery of the target products with as little loss as possible.

What are known as demethanizers, which typically comprise a distillation column, can be used to separate methane. A liquid, methane-rich stream can be charged as reflux at the top of the distillation column. In separation sequences of this type, absorption columns in the form of what are known as C2 absorbers can also be used which are also operated with a liquid, methane-rich stream as reflux. The basic difference between absorption columns and distillation columns is explained below.

For separating product streams of methods for oxidative coupling of methane, it may optionally be possible to dispense with the use of distillation columns, i.e. methods of this type can also be carried out using only absorption columns which, however, as mentioned, also require a liquid, methane-rich stream as reflux. Elsewhere, for example in heat exchangers, a stream of this type can also be used as a liquid refrigerant having a temperature which is significantly below −100° C.

Thus, in the mentioned separation sequences, a product stream from a corresponding method, or at least one stream formed from the product stream, is subjected to a cryogenic treatment (cooling in a heat exchanger, optional separation in a distillation column and/or absorption in an absorption column), in which at least one liquid, methane-rich stream is used.

In separation sequences for product streams of steam cracking processes, the at least one liquid, methane-rich stream is formed from the methane of the product streams. However, this is not the case in methods for oxidative coupling of methane, particularly when, as mentioned, the relatively small amounts of hydrocarbons having two or more carbon atoms are washed out of the product stream only by means of an absorption column. In other words, although a liquid, methane-rich stream is required here, it is not recovered in the separation sequence which is preferably used.

In methods for oxidative coupling of methane, the methane separated from the product stream is advantageously returned into the reactor which is used, thereby achieving a circulation of methane from which methane is removed only due to conversion in the reactor and possibly due to losses during separation.

The removed methane is compensated by a fresh infeed (what is known as a makeup). For example, for this purpose, according to WO 2014/011646 A1 a feed gas containing methane is fed to the inlet side of an appropriate reactor. However, a considerable purification effort is required here to prevent the introduction of disturbing impurities into the reactor.

In view of the above, the object of the present invention is accordingly to improve methods for oxidative coupling of methane.

DISCLOSURE OF THE INVENTION

This object is achieved by a method and an apparatus for producing hydrocarbons by oxidative coupling of methane, having the features of the independent claims. Preferred embodiments are the subject of the dependent claims and of the following description.

Before the features and advantages of the present invention are described, the basic principles thereof and the terms which are used will be explained.

In the presently used context, liquid and gaseous streams can be rich or poor in one or more components, where "rich" can signify a content of at least 50%, 75%, 90%, 95%, 99%, 99.5%, 99.9% or 99.99% and "poor" can signify a content of at most 50%, 25%, 10%, 5%, 1%, 0.1% or 0.01%, on a molar, weight or volume basis. The term "predominantly" can correspond to the definition of "rich". Furthermore, in the present context, liquid and gaseous streams can be enriched with or depleted in one or more components, these terms relating to a corresponding content in a starting mixture from which the liquid or gaseous stream was obtained. The liquid or gaseous stream is "enriched" when it contains at least 1.1 times, 1.5 times, 2 times, 5 times, 10 times, 100 times or 1,000 times the content of a corresponding component, and "depleted" when it contains at most 0.9 times, 0.5 times, 0.1 times, 0.01 times or 0.001 times the content of a corresponding component, based on the starting mixture. Here, the mention of "liquid methane" means a liquid stream which is rich in methane, but which does not have to consist exclusively of methane.

Current methods for separating product streams of methods for producing hydrocarbons include the formation of a number of fractions based on the different boiling points of the components which are contained. Experts use abbreviations therefor, which abbreviations specify the carbon number of the hydrocarbons which are predominantly or exclusively contained in each case. Thus, a "C1 fraction" is a fraction which predominantly or exclusively contains methane (and conventionally possibly also hydrogen which is then also known as "C1 minus fraction"). By contrast, a "C2 fraction" predominantly or exclusively contains ethane, ethylene and/or acetylene. A "C3 fraction" contains predominantly propane, propylene, methylacetylene and/or propadiene. A "C4 fraction" predominantly or exclusively contains butane, butene, butadiene and/or butyne, it being possible for the respective isomers to be contained in different proportions depending on the source of the C4 fraction. The same also applies accordingly to the "C5 fraction" and to the higher fractions. A plurality of such fractions can be combined. For example, a "C2 plus fraction" predominantly or exclusively contains hydrocarbons having two or more carbon atoms and a "C2 minus fraction" predominantly or exclusively contains hydrocarbons having one or two carbon atoms.

In particular the distillation columns and absorption columns which have already been mentioned can be used in the mentioned methods. Reference is made to relevant textbooks with regard to the construction and configuration of appropriate devices (see for example K. Sattler: Thermische Trennverfahren. Grundlagen, Auslegung, Apparate. Weinheim: Wiley-VCH, 3. Edition 2001). In the following, distillation columns and absorption columns are also commonly referred to by the term "separation columns". A separation column used within the scope of the present invention is operated at cryogenic temperatures and is configured for cryogenic gas separation. At least one liquid fraction ("bottom product") and one gaseous fraction ("top product") in an upper region ("top") and a lower region ("bottom") can typically always be removed from a separating column.

In the presently used context, a "distillation column" is a separation column which is configured to separate at least in part a substance mixture (fluid) which is provided in gas or liquid form or in the form of a two-phase mixture having liquid and gaseous portions, optionally also in a supercritical state, i.e. to produce from the substance mixture pure substances or substance mixtures in each case which are enriched with or depleted in or are rich or poor in at least one component compared with the substance mixture within the meaning stated above.

Distillation columns are typically configured as cylindrical metal containers which are equipped with fittings, for example with sieve plates or structured or unstructured packings. A distillation column is distinguished inter alia in that the bottom product is heated by a sump evaporator so that some continuously evaporates and rises in gas form in the distillation column. A distillation column is typically also provided with what is known as a head condenser in which at least some of the top product is liquefied into a condensate and is charged at the top of the distillation column as liquid reflux. Some of the top product obtained from the top gas can be used elsewhere, for example as product.

Unlike a distillation column, an "absorption column" typically does not have a sump evaporator. Absorption columns are also generally known from the field of separation technology. Absorption columns are used for absorption in phase counterflow and are therefore also known as counterflow columns. During absorption in the counterflow, the issuing gas phase flows upwards through an absorption column. Charged from above and removed below, the absorbing solution phase flows against the gas phase. The gas phase is "washed" with the solution phase. Also typically provided in a corresponding absorption column are fittings which ensure a gradual phase contact (plates, spray zones, rotating plates etc.) or a continuous phase contact (random fillings of fillers, packings etc.).

ADVANTAGES OF THE INVENTION

An essential aspect of the present invention is to form the liquid, methane-rich stream, required for the cryogenic treatment of the product stream from a method for the oxidative coupling of methane, not from the product stream itself, but to feed this externally and to use it simultaneously as makeup.

As previously stated, in corresponding methods, the methane contained in the product stream is typically recycled at least in part (in particular is recycled as completely as possible), i.e. a circulation is produced from which only the methane which is respectively converted and is lost due to separation losses is removed. The invention now provides that at least some of the methane which is removed from the circulation is compensated by the methane which is also provided externally for the cryogenic treatment of the product stream.

In this respect, the invention proposes a method for producing hydrocarbons in which a product stream containing hydrocarbons is produced from a methane-rich feed stream and from an oxygen-rich feed stream in a reaction unit which is configured for implementing a method for oxidative coupling of methane, the product stream or at least a stream formed therefrom being treated cryogenically in at least one separation unit using at least one liquid, methane-rich stream.

As previously explained, a "cryogenic treatment" comprises for example a cooling procedure in a heat exchanger, a separation procedure in a distillation column and/or an absorption procedure in an absorption column in which at least one appropriate liquid, methane-rich stream is used.

The method according to the invention also provides that a recycled stream is formed from methane contained in the product stream and from methane contained in the liquid, methane-rich stream in the at least one separation unit. Said recycled stream is fed to the reaction unit as the mentioned methane-rich feed stream. The invention further provides that the liquid, methane-rich stream is provided as makeup. This means that some or all the methane of this liquid, methane-rich stream is not formed from the product stream by separating methane or a methane-containing fraction, i.e. it was not previously contained in the product stream, but rather it originates from an external source, for example from a natural gas pipeline or from a tank. However, the provision as makeup does not exclude the processing of an externally provided stream to recover the liquid, methane-rich stream.

The liquid, methane-rich stream is advantageously produced using a pressurised methane-containing gas mixture which is provided separately from the product stream, for example using pressurised natural gas.

To compensate, as mentioned, for at least some of the methane removed from the circuit, it is advantageously provided that the methane-rich stream is used in an amount in which methane is contained in an amount which is at least as great as the amount of methane converted in the reaction unit. The methane-rich stream can advantageously be used in a greater amount, for example to compensate for separation losses.

Thus, the invention provides the provision of fresh methane which is not or not exclusively in gas form and the feeding thereof into an appropriate reaction unit itself or to the inlet side thereof, as is the case, as mentioned, in WO 2014/011646 A1. In fact, according to the invention, fresh methane, i.e. non-recycled methane is provided at least in part in liquid form, and this methane is fed partly or exclusively to a suitable point in the separation unit. The use of liquid methane makes it possible to prevent the introduction of disruptive impurities into the reactor so that purification is simplified compared with the use of gaseous feed streams. In other words, within the scope of the present invention, fresh methane is fed at least in a part-liquid form into the cold part of an appropriate apparatus, whereas in the prior art it is fed in gas form into the hot part of an appropriate apparatus.

Due to the external provision of liquid methane or of a corresponding methane-rich stream having a defined composition, the invention makes it possible to produce the components of the apparatus of the actual method for oxidative coupling of methane, i.e. a corresponding reaction unit and the associated separation unit, independently of a methane supply. As described, fresh methane is traditionally fed into the reaction unit or upstream thereof and a liquid, methane-rich stream is also required for the separation procedure. The partial or exclusive feeding according to the invention of a liquid, methane-rich stream into the separation unit makes it possible here to create a standardised and parameterisable interface at which methane conforming to specifications (or a corresponding methane-rich stream) is received by the separation unit and at which methane conforming to specifications (or a corresponding methane-rich stream) is transferred by a methane supply. Moreover, the parts of the apparatus operate independently of one another.

If, within the scope of the present invention, a source for a pressurised methane-containing gas mixture is used in which said gas mixture has already been condensed to a suitable pressure, additional condensers are no longer required in order to be able to provide the liquid, methane-rich stream. In any case, a corresponding gas mixture has to be expanded, through which the required coldness and/or shaft power can be produced. Advantageous pressures of this type are present in particular in natural gas pipelines. Non-evaporated liquid natural gas, for example from tankers, can also be used.

The invention reveals particular advantages in the case of the distillation columns and absorption columns which have already been mentioned. By using the liquid, methane-rich reflux which, due to its origin, is substantially free from ethylene, the present invention also makes it possible to advantageously recover fractions which are substantially free from ethylene. The loss of ethylene is thereby minimised using the present invention.

For the mentioned purposes, i.e. a cooling procedure in at least one heat exchanger which is operated with the at least one methane-rich stream as refrigerant and/or a separation procedure in at least one cryogenic separation device (distillation column and/or absorption column) into which the at least one methane-rich stream is charged as reflux, methane must already have been liquefied or must be liquefied, which is why a corresponding minimum pressure is required.

This requirement is satisfied in particular by pressurised natural gas from a corresponding pipeline. Natural gas which is provided in this manner is already at the necessary pressure which allows it to be liquefied and thereby to provide a liquid reflux or a corresponding stream for a heat exchanger. For example, natural gas in corresponding pipelines is at a pressure of 40 to 60 bars, and thus the pressure is significantly above the minimum pressure of at least 28 bars abs. required for liquefaction (at approximately −97° C.). For conventional use as fuel gas, the pressure is traditionally expanded to a pressure of for example less than 9 bars abs. However, according to the invention, correspondingly expanded natural gas is expanded to higher pressures, for example to approximately 36 bars abs. or is used at a correspondingly high pressure.

Before use, an appropriate pressurised, methane-containing gas mixture, for example natural gas is advantageously rid of disruptive components if it does not already satisfy the respective requirements in this regard. The question as to which components are considered to be "disruptive" depends on the desired use, i.e. on the cryogenic treatment which is to be carried out using the at least one methane-rich stream. Lastly, as stated, within the scope of the present application, methane contained in an appropriate liquid, methane-rich stream is transferred into the described circulation and into the reaction unit. Therefore, unlike when the stream is used purely as refrigerant, it is also to be noted that the liquid, methane-rich stream is not only free from water and carbon dioxide and possibly from corrosive constituents, but that said stream also does not contain any components which would accumulate in the circulation and/or which could be harmful in the reaction unit.

The liquid, methane-rich stream is advantageously produced at least in part from a liquid stream which, in turn, is formed from the pressurised methane-containing gas mixture, for example from the natural gas, using a suitable distillation or rectification process. In this manner, the liquid, methane-rich stream can be rid specifically of the mentioned disruptive components, it being possible for the configuration of a corresponding distillation process to be focussed on the purity which is to be achieved. In certain cases, it is possible to dispense with a distillation process, for example when correspondingly pure methane is available. Subject to the required purification procedure, a corresponding pretreatment using condensers, pumps, adsorbers etc. is to be provided, before a distillation or rectification process is optionally carried out.

The pressurised, methane-containing gas mixture is advantageously rid of impurities initially at least partly under pressure. Pressurised purification is particularly advantageous because corresponding purifying devices only have to be configured to treat relatively small volume flows due to condensation. Water and carbon dioxide have to be removed in any case from the methane-containing gas mixture to avoid a freeze-out during and after the subsequent cooling procedure. The further impurities to be removed depend on the later use.

To remove corresponding impurities, for example sulphur compounds, carbon dioxide and/or mercury are advantageously removed at least partly adsorptively from the pressurised, methane-containing gas mixture. To regenerate the adsorbers used in this respect, it is also possible to use a stream resulting from a distillation or rectification process, for example a liquefied top gas (for example nitrogen-containing top gas from a separation column used for providing the liquid, methane-rich stream) or a re-evaporated bottom product.

It is particularly advantageous for the pressurised, methane-containing gas mixture to be depleted in nitrogen, hydrogen and/or helium in the distillation process. It is particularly advantageous to remove components of this type because they may possibly pass into the products or into the described circulation.

The use of a dividing wall column is particularly advantageous in this case. A gas mixture containing methane, nitrogen, hydrogen and/or helium as well as higher hydrocarbons can be fed into a dividing wall column of this type on one side of the dividing wall, while by contrast a liquid gas mixture depleted in higher hydrocarbons and in nitrogen, hydrogen and/or helium is received on the other side of the dividing wall.

The invention also proposes an apparatus which is configured to implement a method, as previously described, and which has all the means configured for implementing a corresponding method. In particular, an apparatus of this type has means for providing the liquid, methane-rich stream and for the provision thereof as makeup. These means include in particular a distillation column, for example a dividing wall column.

The invention will be described in greater detail with reference to the accompanying drawings which show preferred embodiments of the invention.

DETAILED DESCRIPTION OF THE DRAWINGS

Figure 1:
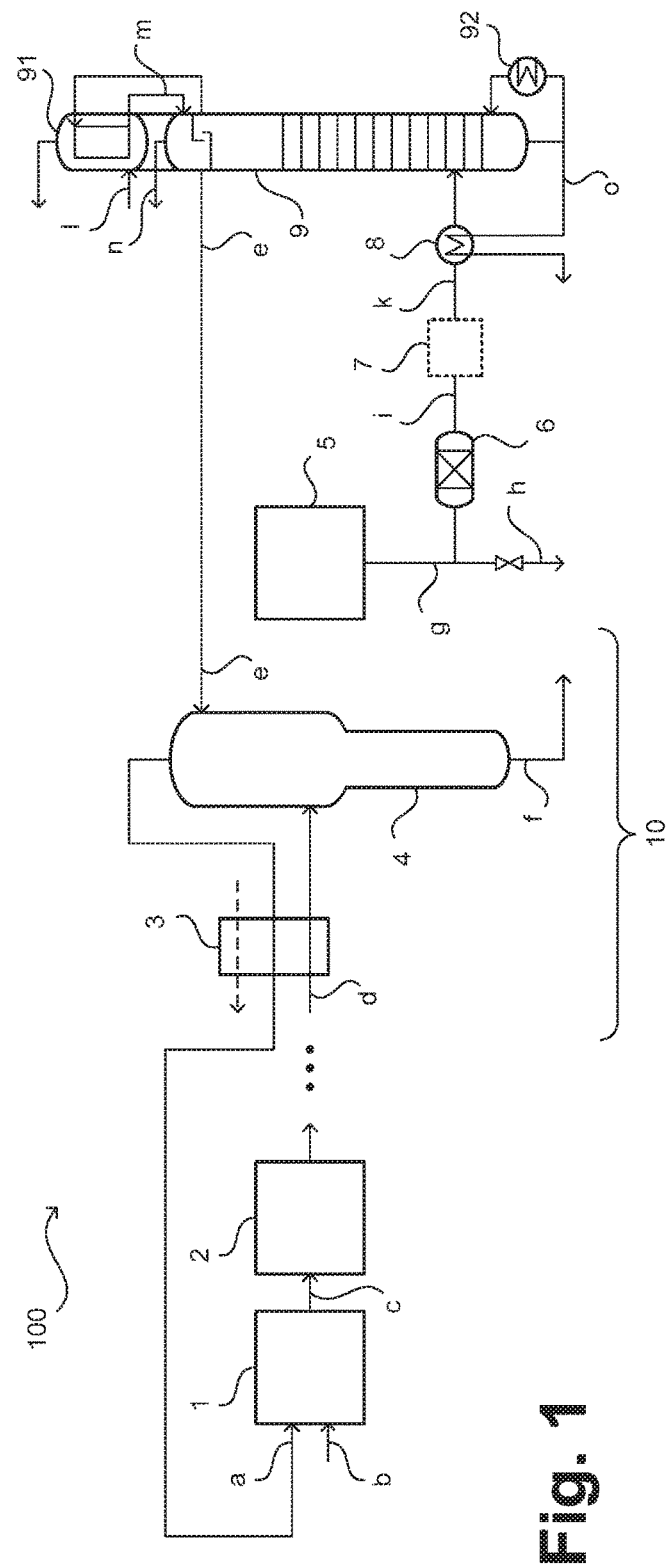
FIG. 1 is a schematic view of an apparatus for producing hydrocarbons according to an embodiment of the invention.

In the figures, identical elements have been shown with the same reference numerals. For the sake of clarity, a repeated description of identical elements is not provided.

FIG. 1 shows an apparatus for producing hydrocarbons using a method for oxidative coupling of methane according to an embodiment of the invention. The apparatus is denoted overall by reference numeral 100. In the illustrated example, the apparatus 100 comprises a reaction unit 1 which is configured for implementing a method for oxidative coupling of methane and comprises for example one or more heated reactors, configured in a manner known per se, having suitable catalysts. The reaction unit 1 can also comprise, for example reaction devices arranged downstream, for example reaction devices for subsequent steam cracking.

Fed to the reaction unit 1 is a methane-rich feed stream a and an oxygen-rich feed stream b, and a product stream c is removed which can have the composition mentioned at the outset (more than 60% methane, less than 10% hydrocarbons having two or more carbon atoms and 10 to 20% of other components such as nitrogen, argon, hydrogen, carbon monoxide and/or carbon dioxide). This product stream undergoes one or more processing steps, for example a water wash, amine scrubbing, an adsorptive purification, one or more drying steps, condensation, cooling etc. Corresponding steps are summarised here by block 2. Further steps, as shown here by suspension marks, can be provided.

A correspondingly processed stream which is freed in particular from water and carbon dioxide and is now denoted by d is fed to a separation unit, collectively denoted by 10 and is cooled therein in a heat exchanger 3 and is fed into an absorption column 4. Charged onto the absorption column 4 is a liquid, methane-rich stream e as reflux. The absorption column 4 is operated such that in the bottom thereof, a mixture predominantly or exclusively containing hydrocarbons having two or more carbon atoms is separated which can be removed as stream f. A mixture which is free or almost free from hydrocarbons having two or more carbon atoms or also pure or almost pure methane is removed as stream a at the top of the absorption column 4.

Instead of a single absorption column 4, it is also possible to use any other suitable unit capable of recovering a mixture which predominantly or exclusively contains hydrocarbons having two or more carbon atoms which can be removed as stream f and is capable of recovering a mixture which is free or almost free from hydrocarbons having two or more carbon atoms or pure or almost pure methane which can be removed as stream a. For example, combined units consisting of a part operating by absorption and a part operating by distillation, configured as a double column, or two separate columns can be used. The configuration and implementation in terms of apparatus depend on the contents of the individual components of stream d. It is crucial that the mixture of stream a or the pure or almost pure methane of this stream a is free or almost free from hydrocarbons having two or more carbon atoms. The mixture of stream f can contain certain amounts of methane. Due to the use of absorption column 4 or of an appropriate other unit, the components which are later contained in stream a do not have to be condensed in order to form a corresponding stream a. Therefore, corresponding components can be returned directly to the reaction unit 1. The absorption column 4 or a corresponding unit can be operated at pressures of less than 30 bars, for example at 13 to 17 bars, more generally at pressures which result in a temperature of the top of the absorption column 4 or of a corresponding unit of below −97° C. In this way, stream a no longer contains any or contains almost no hydrocarbons having two or more carbon atoms.

According to the embodiment of the invention shown here, stream e is formed using a pressurised, methane-containing gas mixture, denoted here by g. Stream g is provided, for example via a natural gas supply 5, in particular by a pipeline. The pressurised, methane-containing gas mixture of stream g is for example in a natural gas pipeline at a pressure of 40 to 60 bars and is thus capable of liquefaction, if appropriate after previous expansion.

Some of the pressurised, methane-containing gas mixture of stream g can be expanded, for example as stream h, by a valve (not shown) to a pressure of less than 9 bars and can then be used as fuel gas. The remainder is delivered to a preparation procedure which operates for example at a pressure of 10 to 50 bars, for example at 20 to 45 bars or at 30 to 40 bars. In any case, the pressure is below the critical pressure of methane.

Appropriate gas mixtures from pipelines, such as the pressurised, methane-containing gas mixture of stream g, still typically contain traces of impurities such as sulphur compounds, carbon dioxide and mercury. Impurities of this type can be removed in an adsorptive purification device 6 in which for example streams n and o, which are described below, can also be used for regeneration.

A correspondingly purified stream i can undergo any desired further processing steps 7, for example the removal of carbon dioxide or drying. The further processed stream, now denoted by k, is then cooled in a heat exchanger 8 and transferred to a distillation column 9 at a suitable height. The distillation column 9 is used to recover a methane-rich top stream from the methane-containing, pressurised gas mixture of streams f and k. If stream k already has an adequate purity, i.e. in particular if it already has an adequate methane content, pure liquefaction without the use of a distillation column 9 is also possible.

A gaseous top stream can be drawn off from the distillation column 9, liquefied through the condensation chamber of a head condenser 91 which is operated with a suitable refrigerant stream l and is recharged at least in part as stream m at the top of the distillation column 9. Methane which is not liquefied in the head condenser 91 of the distillation column 9 can be drawn off as stream n and for example can be used, as mentioned, for regeneration purposes. Stream e, which has already been described and which substantially consists of liquid methane, can be removed at the top of the distillation column 9 by a suitable liquid removal device (not shown) or can be drawn off from the head condenser 91 or from a corresponding container. It is understood that the invention can be used employing different types of head condensers, for example external head condensers comprising distinct separator containers.

A liquid fraction which can consist predominantly of hydrocarbons having two or more carbon atoms separates in the bottom of the distillation column 9. However, it is also possible to operate the distillation column 9 such that a gas mixture also containing further components to be separated separates in the bottom of the column. The bottom of the distillation column 9 can also still contain a considerable amount of methane. It is important that a fraction which allows the above-described use and which only has corresponding components is formed at the top of the distillation column 9.

A stream o which is removed from the bottom of the distillation column 9 and is not evaporated in a sump evaporator 92 of the distillation column 9 can also be used as fuel gas, and therefore the composition thereof is less critical compared to stream m. As shown, the heat exchanger 8 can also be operated with a stream removed from the bottom of the distillation column 9. It is also possible, if appropriate, to dispense with a sump evaporator 92.

The distillation column 9 can be operated under differing conditions which can also depend on the specific gas composition which is present. For example, pressures of from 13 to 36 bars or from 28 to 36 bars can be used.

Drawn off from the top of the absorption column is a stream a which preferably contains the predominant proportion of the methane contained in product stream c and in the liquid, methane-rich stream e. This stream is used as the methane-rich feed stream a. Thus, in the illustrated example, it is provided to only use stream e, which has been mentioned several times, to make up the methane. Stream e originates from the separately provided, methane-containing gas mixture of stream g which is processed appropriately.

Figure 2:
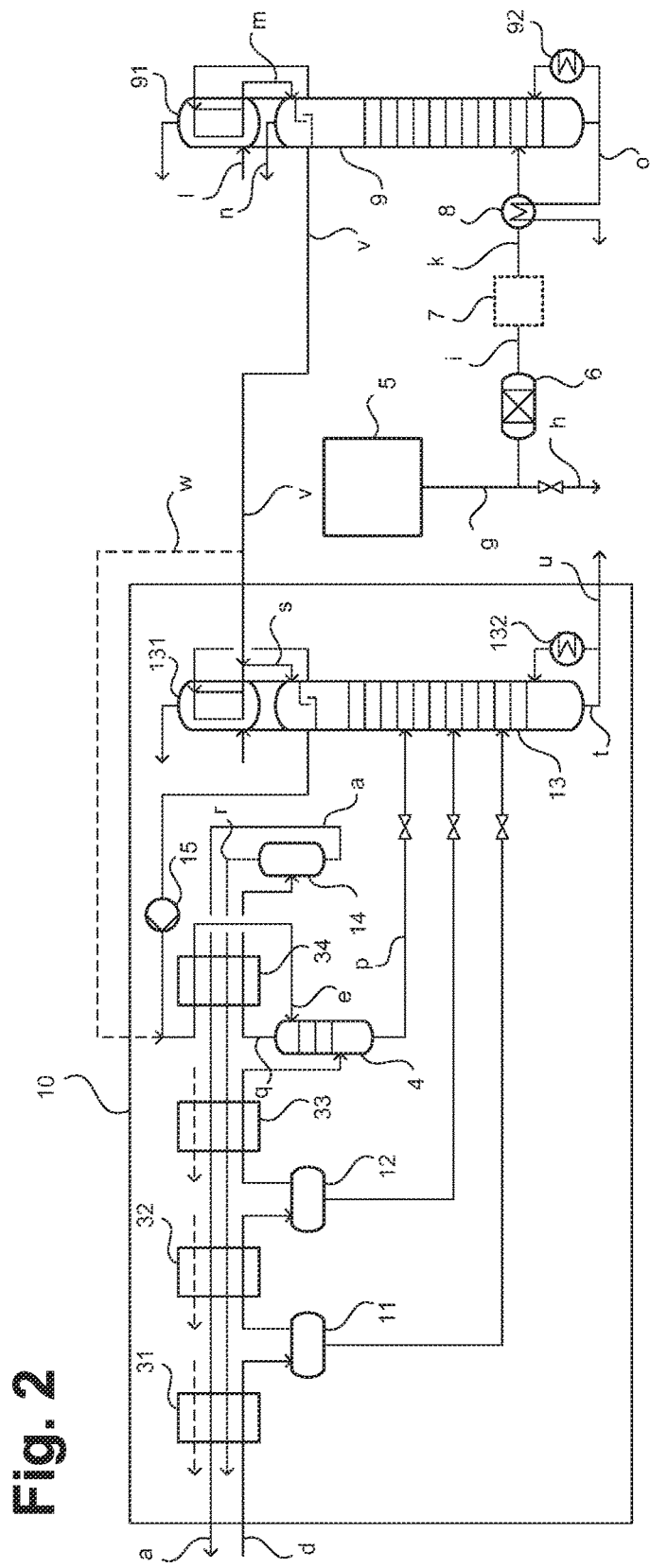
FIG. 2 is a schematic view of an apparatus for producing hydrocarbons according to an embodiment of the invention.

FIG. 2 shows an apparatus for producing hydrocarbons using a method for oxidative coupling of methane according to a further embodiment of the invention. The reaction unit 1 has not been shown here, only streams a and d corresponding to FIG. 1 are shown.

The separation unit 10 of the apparatus shown in FIG. 2 corresponds to a demethanizer of a steam cracking process. The separation unit 10 is shown in a greatly simplified form. A plurality of streams, valves, heat exchangers, containers etc., have not been shown. The separation unit comprises four (counterflow) heat exchangers 31 to 34, but it can also have more or fewer corresponding heat exchangers and further heat exchangers. The heat exchangers 31 to 34 can be cooled in particular using suitable refrigerant streams, shown here in dashed lines, in addition to the streams described in the following.

Stream d is guided through the heat exchanger 31, is cooled therein and is then fed into a liquid separator 11. Here, fluid which remains as gas is guided through the heat exchanger 32, is cooled and fed into a liquid separator 12. Here as well, fluid remaining as gas is guided through the heat exchanger 33, is further cooled and transferred to an absorption column 4 at for example approximately 35 bars abs. and at approximately −100° C.

Here as well, a liquid methane-rich stream e is charged at the head of the absorption column 4 and washes out hydrocarbons having two or more carbon atoms into the bottom of the absorption column. However, in the illustrated example, the absorption column 4 is operated such that separated in the bottom of the column is a mixture which still contains considerable amounts of methane in addition to hydrocarbons having two or more carbon atoms. This mixture is removed as stream p and is expanded in a distillation column 13. In typical methods for processing streams from steam cracking processes, condensates from the separator containers 11 and 12 are also expanded in said distillation column. This can also be the case in methods for oxidative coupling of methane, but is not necessarily provided here.

Drawn off from the top of the absorption column 4 is a stream q substantially consisting of methane and hydrogen. This stream is cooled in the heat exchanger 34 to a temperature below the boiling temperature of methane at the used pressure and is transferred to a hydrogen separator 14 in which substantially pure methane is separated as liquid. This alone is used as the methane-rich feed stream a, whereas hydrogen as stream r is used elsewhere, for example for hydrogenation purposes.

The distillation column 13 is operated in such a way that a methane-rich top gas, preferably substantially pure methane accumulates at the top of the column. This is drawn off, passed through a condensation chamber of a head condenser 131 which is operated using a suitable refrigerant stream in the evaporation chamber thereof and is charged onto the distillation column 13 in the form of stream s as liquid reflux. Some of the liquefied stream s can be drawn off, brought to the pressure of the absorption column 4 by a pump 15 and used as reflux in the form of the mentioned stream e. It is stressed explicitly that streams s and e can also be recovered in a different manner, for example by means of external separator containers and/or external head condensers.

It is possible to remove from the bottom of the distillation column 13 a low-methane stream t which contains the predominant proportion of the hydrocarbons, contained in stream d, having two or more carbon atoms. Part of stream t can be evaporated in a sump evaporator 132 of the distillation column 13 and reintroduced into said column, a further part is removed as stream u and can be directed out of the apparatus after any desired optional intermediate steps.

Thus, in the embodiment shown in FIG. 2, stream e is not necessarily provided directly externally, it can also initially at least be partly formed from methane from the distillation column 13 or from the head condenser 131 thereof. Nevertheless, here as well methane is provided externally, namely as stream v. Stream v is obtained in the same manner as stream e which was described with regard to FIG. 1. Therefore, reference is made to the above details. A partial stream w of stream v can also be used for cooling purposes.

However, stream v can also be guided in its entirety in the same manner as illustrated stream w.

A dividing wall column can also be used instead of the single distillation column 9. The use of a dividing wall column takes into account the fact that for example natural gas, which is provided as the pressurised, methane-containing gas mixture of stream g, typically contains considerable amounts of nitrogen. To prevent said nitrogen from passing into stream e or v, nitrogen is depleted in the dividing wall column. Otherwise, said nitrogen could contaminate products of a corresponding apparatus. Nitrogen could also be fed into the circulation, which circulation has been described several times, and could accumulate in the circulation if it is not converted in the reaction unit 1.

Figure 3:
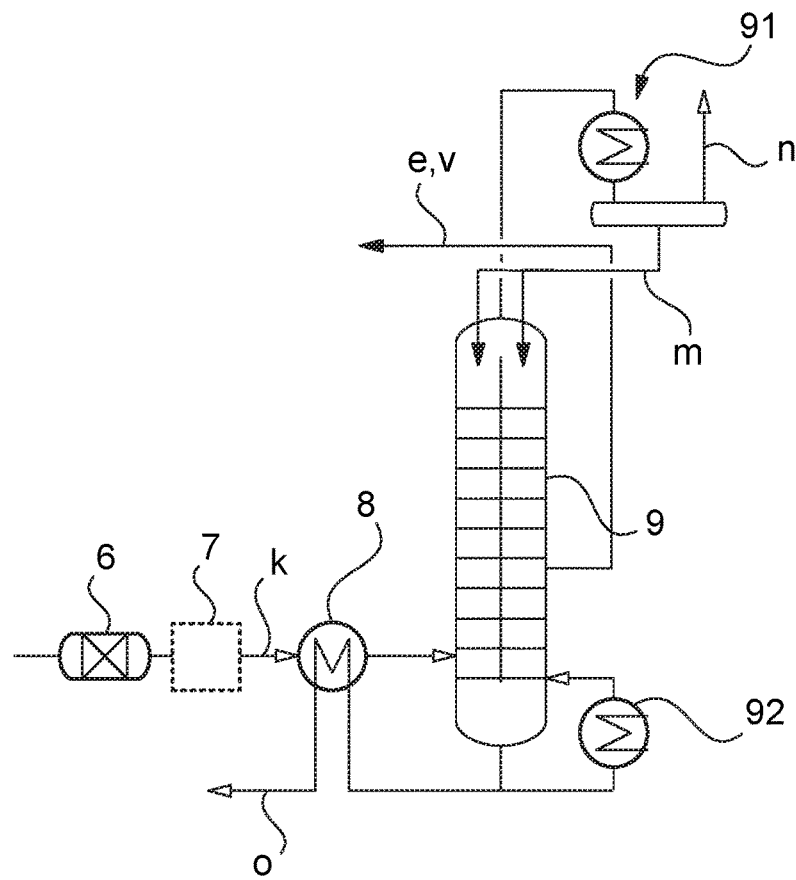
FIG. 3 is a schematic partial view of an apparatus for producing hydrocarbons according to an embodiment of the invention.

FIG. 3 shows a detail of an apparatus according to the invention in which a corresponding dividing wall column is denoted by 9 in the same manner as the standard distillation column 9 in FIGS. 1 and 2. Incorporation emerges from the denotation of the respective streams. In the example shown, the dividing wall column 9 comprises a head condenser 91 and a sump evaporator 92. After being cooled in the heat exchanger 8, the gas stream k which still contains nitrogen is fed into a region of the dividing wall column 9, shown here on the left. In a region of the dividing wall column 9, shown on the right, nitrogen-depleted methane can be removed and used as stream e (corresponding to FIG. 1) or as stream v (corresponding to FIG. 2).

Figure 4:
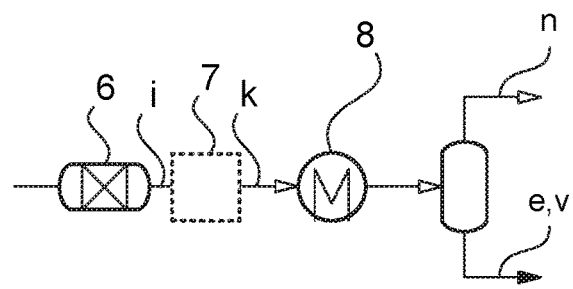
FIG. 4 is a schematic partial view of an apparatus for producing hydrocarbons according to an embodiment of the invention.

FIG. 4 shows a particularly simple variant. Here, stream e or v is merely obtained through liquefaction of an appropriately purified stream k or i. This variant is suitable for cases in which the gas mixture of stream g already has a composition conforming to specifications. If stream g is already free from other disruptive impurities, it is also possible to dispense with the purifying device 6.

The invention claimed is:

1. A method for producing hydrocarbons by oxidative coupling of methane comprising:
    contacting a methane-rich feed stream and an oxygen-rich feed stream in a reaction unit configured for oxidative coupling of methane to produce a product stream comprising hydrocarbons and unreacted methane;
    cryogenically separating the product stream in at least one separation unit using at least one liquid, methane-rich stream to form a recycle stream comprising unreacted methane and at least a portion of methane contained in the at least one liquid, methane-rich stream; and
    feeding the recycle stream to the reaction unit, wherein the methane-rich feed stream consists of the recycle stream and the methane-rich feed stream is the only methane feed to the reaction unit;
    wherein the at least one liquid, methane-rich stream is produced using a pressurised, methane-containing gas mixture that is provided separately from the product stream and wherein the liquid, methane-rich stream is used in an amount that is greater than or equal to the amount of methane which is converted in the reaction unit and which is lost by separation losses.

2. The method according to claim 1, wherein the cryogenic separation comprises a cooling procedure in at least one heat exchanger which is operated with the at least one liquid, methane-rich stream as refrigerant.

3. The method according to claim 1, wherein the cryogenic separation comprises a separation procedure in a cryogenic separation device in which the at least one liquid, methane-rich stream is charged as reflux.

4. The method according to claim 3, wherein an absorption column and/or a distillation column is used as the cryogenic separation device.

5. The method according to claim 1, wherein natural gas is used as the pressurised, methane-containing gas mixture.

6. The method according to claim 1, wherein the liquid, methane-rich stream is produced at least in part from a liquid stream which is formed from the pressurised, methane-containing gas mixture using a distillation process.

7. The method according to claim 6, wherein the pressurised, methane-containing gas mixture is at least partly rid of impurities before the distillation process is carried out.

8. The method according to claim 7, wherein sulphur compounds, carbon dioxide and/or mercury are at least partly removed from the pressurised, methane-containing gas mixture.

9. The method according to claim 6, wherein the pressurised, methane-containing gas mixture is depleted in nitrogen, hydrogen and/or helium in the distillation process.

10. The method according to claim 9, wherein a dividing wall column is used to deplete the pressurised, methane-containing gas mixture in nitrogen, hydrogen and/or helium in the distillation process.

* * * * *